United States Patent
Levine

(10) Patent No.: US 7,559,936 B2
(45) Date of Patent: Jul. 14, 2009

(54) CARDIAC DEVICES AND METHODS FOR PERCUTANEOUS REPAIR OF ATRIOVENTRICULAR VALVES

(75) Inventor: Robert A. Levine, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 912 days.

(21) Appl. No.: 10/640,974

(22) Filed: Aug. 13, 2003

(65) Prior Publication Data

US 2004/0122448 A1    Jun. 24, 2004

Related U.S. Application Data

(60) Provisional application No. 60/403,073, filed on Aug. 13, 2002.

(51) Int. Cl.
*A61B 17/10* (2006.01)
*A61B 17/08* (2006.01)

(52) U.S. Cl. ........................ 606/139; 606/213

(58) Field of Classification Search ........... 606/139, 606/144, 148, 53, 219, 142, 205, 52, 1; 128/898; 600/104; 604/523, 528, 530–532
See application file for complete search history.

(56) References Cited

U.S. PATENT DOCUMENTS

| | | | | |
|---|---|---|---|---|
| 4,686,965 A | * | 8/1987 | Bonnet et al. | 600/104 |
| 5,395,367 A | * | 3/1995 | Wilk | 606/1 |
| 6,129,758 A | | 10/2000 | Love | 623/2.11 |
| 6,165,183 A | | 12/2000 | Kuehn et al. | 606/139 |
| 6,269,819 B1 | | 8/2001 | Oz et al. | 128/898 |
| 6,312,447 B1 | * | 11/2001 | Grimes | 606/219 |
| 6,352,503 B1 | * | 3/2002 | Matsui et al. | 600/104 |
| 6,355,030 B1 | | 3/2002 | Aldrich | |
| 6,402,679 B1 | | 6/2002 | Mortier et al. | |
| 6,432,039 B1 | | 8/2002 | Wardle | |
| 6,461,366 B1 | * | 10/2002 | Seguin | 606/144 |
| 6,530,913 B1 | * | 3/2003 | Giba et al. | 604/523 |
| 6,540,666 B1 | | 4/2003 | Chekanov | |
| 6,575,971 B2 | | 6/2003 | Hauck et al. | 606/52 |
| 6,626,930 B1 | * | 9/2003 | Allen et al. | 606/219 |

(Continued)

FOREIGN PATENT DOCUMENTS

WO    9635469    11/1996

(Continued)

OTHER PUBLICATIONS

Robert A. Levine et al., "Ischemic Mitral Regurgitation on the Threshold of a Solution from Paradoxes to Unifying Concepts", Contemporary Reviews in Cardiovascular Medicine, 2005; 112, pp. 745-758.

(Continued)

*Primary Examiner*—Julian W Woo
(74) *Attorney, Agent, or Firm*—Dorsey & Whitney LLP

(57) ABSTRACT

Novel apparatus and minimally invasive methods to treat The present invention provides methods and devices for grasping, stabilizing and fastening of cardiac valve leaflets to treat atrioventricular valve regurgitation, particularly mitral valve regurgitation, in the context of prolapse and/or flail mitral valve. Independent leaflet grasping elements provide the ability to reposition the leaflets for fastening and enough stability to prevent leaflet movement during fastening.

12 Claims, 10 Drawing Sheets

U.S. PATENT DOCUMENTS

| | | |
|---|---|---|
| 6,629,534 B1 | 10/2003 | St. Goar et al. |
| 6,695,866 B1 * | 2/2004 | Kuehn et al. ............... 606/139 |
| 6,752,813 B2 * | 6/2004 | Goldfarb et al. ............ 606/139 |
| 6,770,083 B2 | 8/2004 | Seguin |
| 2002/0013571 A1 | 1/2002 | Goldfarb et al. ............... 606/1 |
| 2002/0029060 A1 | 3/2002 | Hogendijk |
| 2002/0161378 A1 | 10/2002 | Downing ................... 606/108 |
| 2003/0120341 A1 | 6/2003 | Shennib et al. |

FOREIGN PATENT DOCUMENTS

| | | |
|---|---|---|
| WO | 9913777 | 3/1999 |
| WO | 0060995 | 10/2000 |
| WO | WO 00/60995 A2 | 10/2000 |
| WO | WO 00/60995 A3 | 10/2000 |
| WO | 0128432 | 4/2001 |
| WO | 2004002364 | 1/2004 |
| WO | 2004012583 | 2/2004 |

OTHER PUBLICATIONS

Judy Hung et al., "Reverse Ventricular Remodeling Reduces Ischemic Mitral Regurgitation Echo-Guided Device Application in the Beating Heart", Circulation, Nov. 12, 2002, pp. 2594-2600.

Judy Hung et al., "Mechanism of Recurrent Ischemic Mitral Regurgitation After Annuloplasty continued LV remodeling as a moving target", Circulation, Sep. 14, 2004, pp. 85-90.

Emmanuel Messas et al., "Chordal Cutting A New Therapeutic Approach for Ischemic Mitral Regurgitation", Ischemic Mitral Regurgitation, Jul. 2001, pp. 1958-1963.

Emmanuel Messas et al., "Efficacy of Chordal Cutting to Relieve Chronic Persistent Ischemic Mitral Regurgitation", Circulation, Sep. 9, 2003, pp. 111-115.

International Search Report for International application No. PCT/US03/24367.

European Search Report for European Patent Application No. EP 03 76 7158.

International Search Report for International Application No. PCT/US03/20450.

* cited by examiner

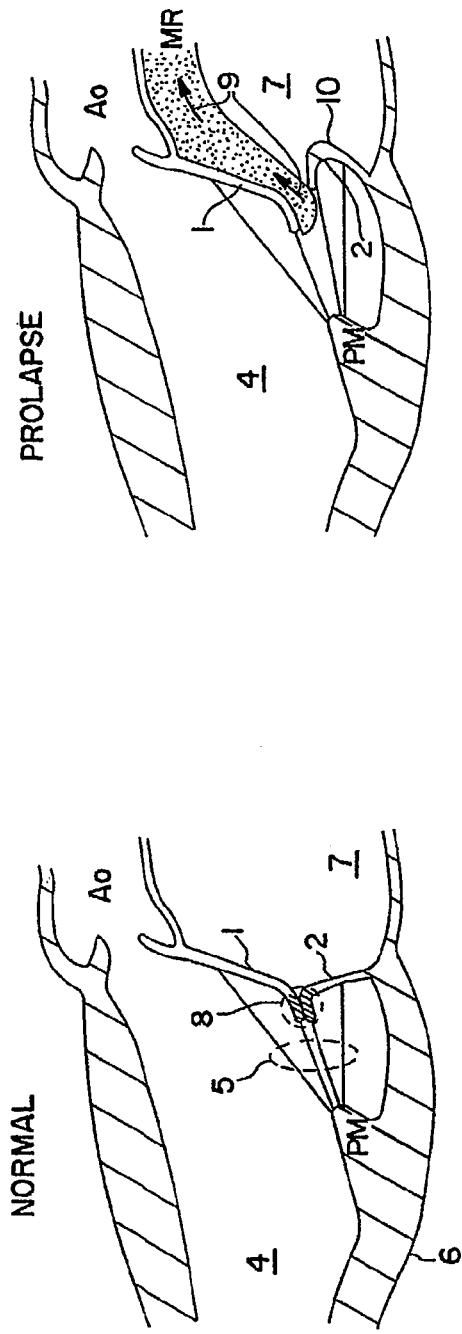
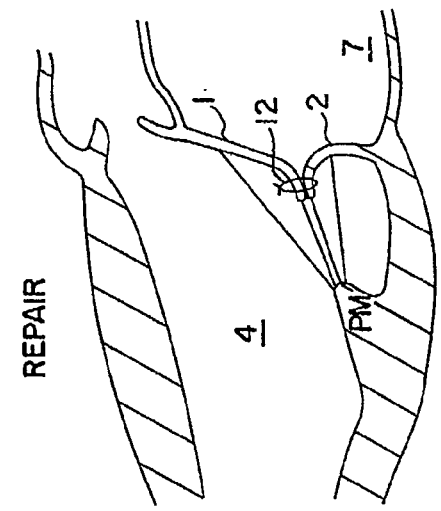
FIG. 1A NORMAL
FIG. 1B PROLAPSE
FIG. 1C PRIOR ART REPAIR

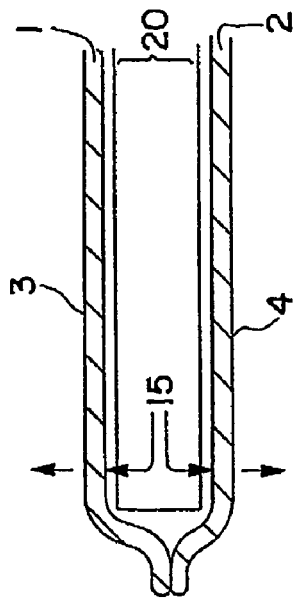
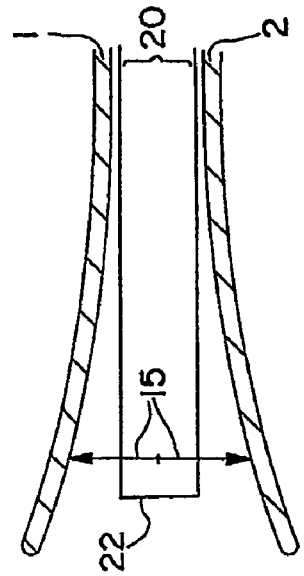
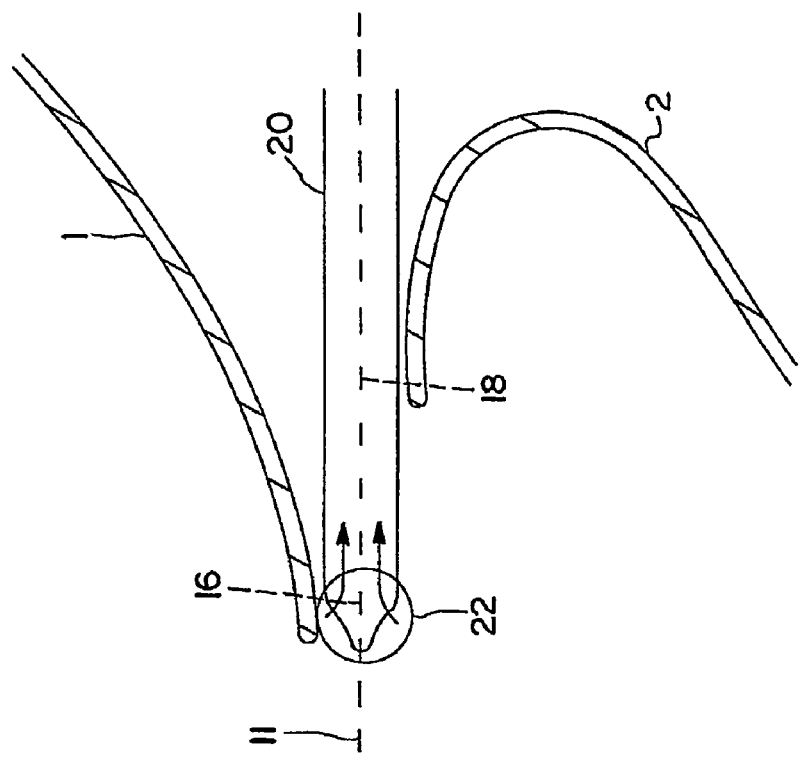

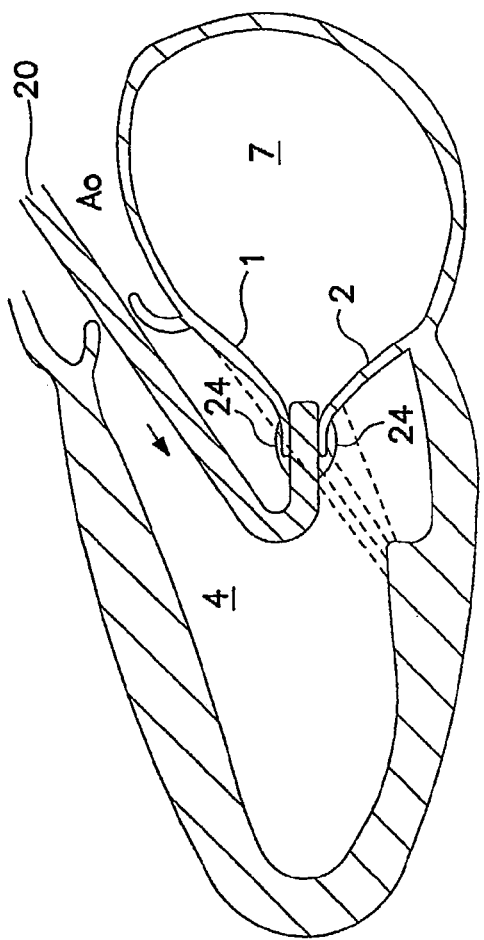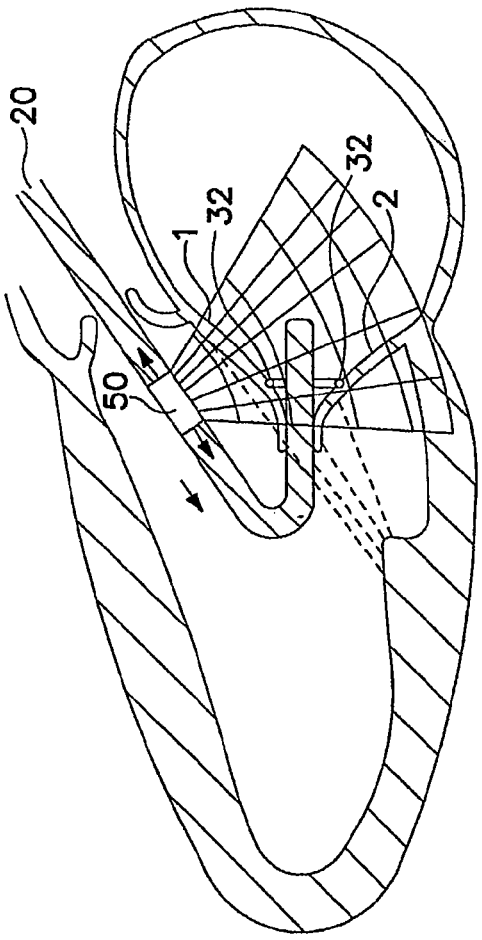

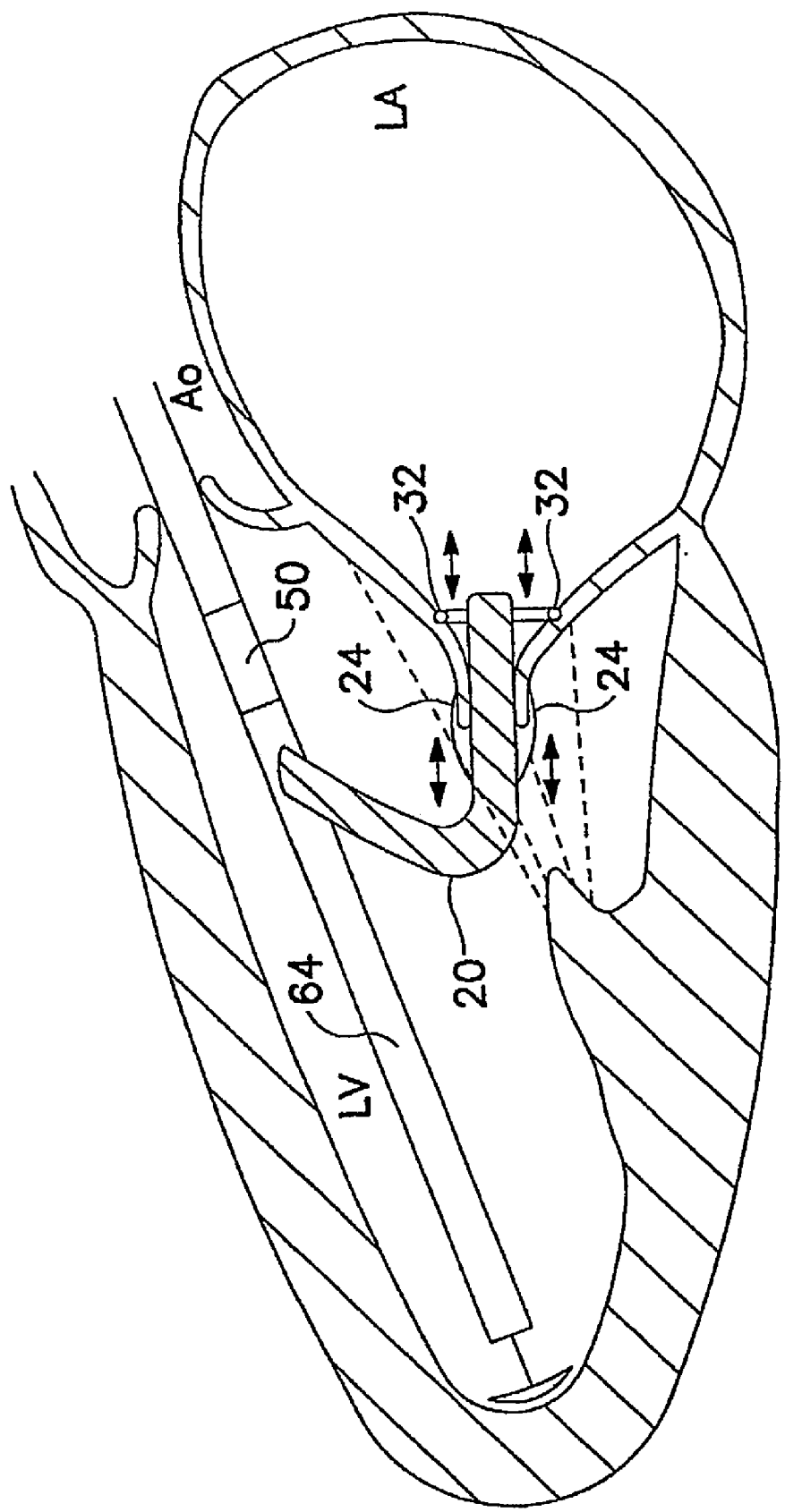

CARDIAC DEVICES AND METHODS FOR PERCUTANEOUS REPAIR OF ATRIOVENTRICULAR VALVES

The present application claims the benefit of priority to U.S. Provisional Application 60/403,073, entitled "Devices and Methods for Percutaneous Mitral Valve Repair", filed Aug. 13, 2003, the contents of which are incorporated herein by reference.

FIELD OF THE INVENTION

The present invention relates generally to devices (i.e., articles of manufacture, apparatus, systems, instruments) and methods for treating heart disease and, in particular, to devices and methods for minimally invasive repair of atrioventricular valve regurgitation (MR) occurring in the context of mitral valve prolapse (MVP), flail mitral valve, and/or ischemic MR.

BACKGROUND OF THE INVENTION

A mitral valve, such as shown in FIG. 1A, including an anterior leaflet 1 and a posterior leaflet 2, is the inlet valve to the main heart pumping chamber (left ventricle 4). The mitral valve is forced to close when the ventricle 4 contracts, preventing backward flow of blood. To ensure that this valve does not prolapse backward (into left atrium 7) when the heart contracts, leaflets 1,2 are restrained by a network of tendinous chords 5 anchored to the posterior wall of the heart 6. The leaflets normally meet or coapt so that their tips are juxtaposed, along with up to one-third of their lengths, forming an effective seal 8 to prevent MR. In a variety of diseases, however, the leaflets fail to meet properly due to leaflet elongation or elongation or rupture of the chords 5. As shown in FIG. 1B, one or more leaflet portions 10 may then prolapse into the left atrium 7, reducing coaptation and creating a gap between the leaflets 1,2 that allows MR to occur (blood flow illustrated by arrows 9.). Such regurgitation can produce heart failure, rhythm disorders, sudden death, and a predisposition to lethal heart valve infections. Therapy has until now required open-heart surgery to replace the valve or repair it by approximating leaflet tips.

Alfieri, et. al, have described a possibly minimally invasive repair mechanism. As shown in FIG. 1C, a suture 12 may be placed between the tips of the leaflets 1,2 to prevent prolapse of one leaflet relative to the other. As shown in FIG. 1D, this produces a competent valve with two openings 14, one on each side of the suture 12 position. Such an orifice does not materially obstruct inflow of blood into the left ventricle.

Several approaches have been proposed to practice this repair in a minimally invasive manner. Specifically, Grimes (U.S. Pat. No. 6,312,447) teaches that a catheter, advanced across the interatrial septum into the left atrium, can grasp the leaflet tips using a suction apparatus at the end of the catheter. A fastener such as a staple or shape memory rivet is then inserted into the leaflet tips to effect the edge-to-edge closure repair.

Previous approaches employing suctioning and/or suturing of leaflet tips suffer from a number of common limitations. First and foremost, as shown in FIG. 2A, in patients with sufficient MR to warrant such procedure, the leaflets 1,2 are initially misaligned, limiting or precluding the ability of a single device 22 alone at the tip of a catheter 20, or multiple devices at a single location along the catheter center axis 11, to bring the leaflet tips, at spatially distinct positions 16 and 18, into juxtaposition in order to suture or fasten them together. Second, in order to be effective, a suction device for grabbing the leaflet tips must withdraw blood extremely rapidly. Unless blood is reinfused immediately, this can cause hypotension. Third, as illustrated in FIG. 2B, unless an additional mechanism is inserted via the aorta to stabilize leaflet surfaces 3 and 4 that are not adjacent to the suction device, a rivet or staple 15 emerging from the catheter 20 may simply displace the leaflets 1,2 from the catheter tip 22 (as shown in FIG. 2C) rather than successfully penetrate the leaflets. Fourth, approaches that employ grasping the leaflets generally do so in a plane perpendicular to the catheter, and do not provide a sufficiently large and stable leaflet surface area through which a staple or a suture can be inserted.

Thus, what is needed is a percutaneous mitral (or tricuspid) valve repair system that can overcome these and other limitations of the prior art. A single device accomplishing all of the above objectives and others is highly desirable.

SUMMARY OF THE INVENTION

The present invention provides novel devices and minimally invasive methods to treat heart disease related to mitral valve regurgitation occurring in the context of cardiac valve prolapse. The present invention allows for independent capture and repositioning of mitral leaflets regardless of whether they are aligned, and provides a stabilized large leaflet surface area through which sutures, staples, rivets and the like may be inserted. Use of a novel percutaneous catheter and other novel devices disclosed herein enables therapeutic maneuvers that do not require opening the chest or heart, however the present invention is not limited to percutaneous approaches. In the description that follows, the several specific preferred embodiments of the present invention referring to the invention's applicability to the mitral valve are meant in no way to be limiting. It will be readily appreciated that the present invention may additionally be effectively applied to leaflets of the tricuspid valve.

In a first aspect, the present invention provides a device and a method of use thereof to repair a mitral valve, comprised of a catheter assembly for delivering in a minimally invasive manner a pair of maneuverable grasping elements that are independently translatable through the catheter assembly to a position near the mitral valve. The grasping elements are reversibly and radially extendable from the catheter assembly so as to capture and stabilize portions of two valve leaflets in an apposed position so that a fastening mechanism (e.g., a staple, rivet or the like) which is also translated through the catheter assembly may be used to affix portions of the anterior and posterior leaflets to one another.

In one embodiment, the catheter assembly comprises a single catheter, that may be substantially straight for an antegrade approach, or alternatively may have a curved distal end so as to enable valve access retrograde via the aorta. Shape memory materials, such as nickel titanium (e.g., NITINOL™ www.nitinol.com) may be used to manufacture several components of the present invention, including the curved distal end of the catheter assembly. The fastening mechanism and grasping elements are optionally composed of shape memory material as well.

In another embodiment, the catheter assembly comprises a pair of slidably linked catheters, each of which is responsible for delivering a grasping element to the mitral valve region.

The fastening mechanism is radially extendable and disengagable from the catheter assembly through at least one side port of the catheter assembly. Described below is a mechanism by which the fastening mechanism may be disengaged from the catheter assembly after insertion through the leaflets, which occurs, significantly, without displacing the captured leaflets in a direction away from the catheter assembly and each other.

In one embodiment, the grasping elements extend from the distal end of the catheter assembly with reverse deformation so as to clip the ventricular side of the valve leaflets. In an alternative, but not mutually exclusive embodiment, the grasping elements extend from side ports in the catheter assembly and are steered so as to be able to grasp the atrial sides of the leaflets. In a preferred embodiment, two pairs of grasping elements are employed to grasp both sides of both the posterior and anterior leaflets. Various embodiments of the grasping elements are described below, including clip-like configurations and embodiments having operable jaws disposed at the ends of each grasping element.

In certain embodiments, the operation of each grasping element is triggered by sensors for detecting contact and/or proximity of the leaflet to be grasped to the grasping elementl.

External or internal cardiac imaging of the region of the mitral valve may be employed to facilitate proper positioning of the grasping elements and/or monitoring of effectiveness of the procedure. This imaging can alternatively be achieved through the use of ultrasound, magnetic resonance or fiber optics.

For a better understanding of the present invention, reference is made to the accompanying drawing and detailed description. The scope of the present invention will be pointed out in the appended claims.

BRIEF DESCRIPTION OF THE DRAWING

The advantages of the present invention will be apparent in the following detailed description of the illustrative embodiments thereof, which is to be read in connection with the accompanying drawing, wherein:

FIGS. 1A-1C are illustrations of a portion of a human heart showing normal, prolapsed and repaired mitral leaflet closure, diagrammed in a long-axis view of the left ventricle, as would be viewable by ultrasound imaging;

FIG. 2A is a side view illustration of a cardiac valve demonstrating a limitation of a prior art catheter suctioning approach to grasping leaflets at different positions along a catheter due to prolapse;

FIGS. 2B-2C are side view illustrations of a cardiac valve demonstrating the displacement of mitral leaflets encountered by prior art approaches to valve stapling;

FIG. 6A is an illustration of a retrograde catheter insertion with grasping elements grasping the ventricular surfaces of the leaflets;

FIG. 6B is an illustration of a retrograde catheter insertion with grasping elements grasping both atrial and ventricular surfaces of the leaflets under imaging guidance;

FIGS. 7A-7B are illustrations of embodiments of catheter stabilization mechanisms in accordance with the present invention.

DETAILED DESCRIPTION OF PREFERRED EMBODIMENTS OF THE INVENTION

Figure 1D:
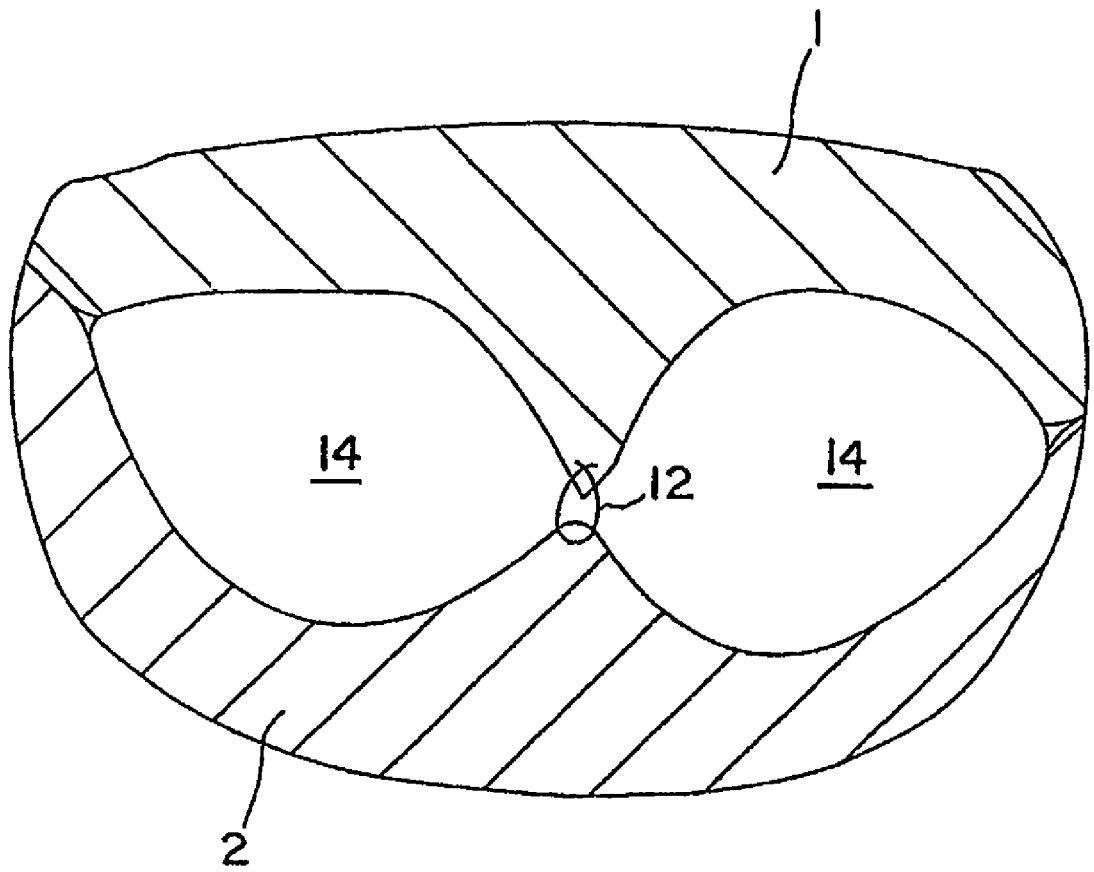
FIG. 1D is an illustration of the mitral leaflets after repair, as viewable from the left atrial perspective with the valve open when the heart relaxes.

Preferred embodiments of the present invention will now be described with reference to the several figures of the drawing.

Numerous embodiments of the present invention will now be described in the context of mitral valve prolapse. Devices in accordance with the present invention are characterized in that they permit the anterior and posterior leaflets to be separately grasped and independently translated along an axis of a catheter assembly until leaflet apposition is achieved for the purpose of fastening the leaflets to one another. Use of the devices is not, however, limited to the mitral valve, as use on the tricuspid or any other cardiac valve will be readily appreciated by artisans.

Figure 3B:
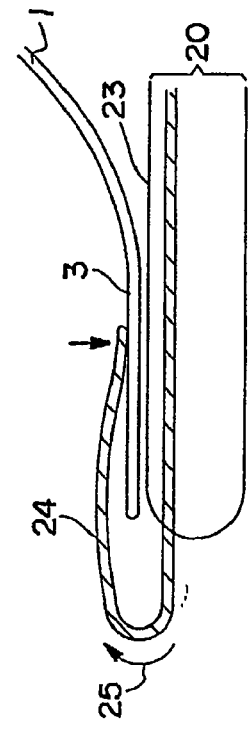
FIGS. 3A-3B are side view illustrations of a cardiac leaflet being grasped on its ventricular surface by a grasping element in accordance with one embodiment of the present invention.
Figure 3C:
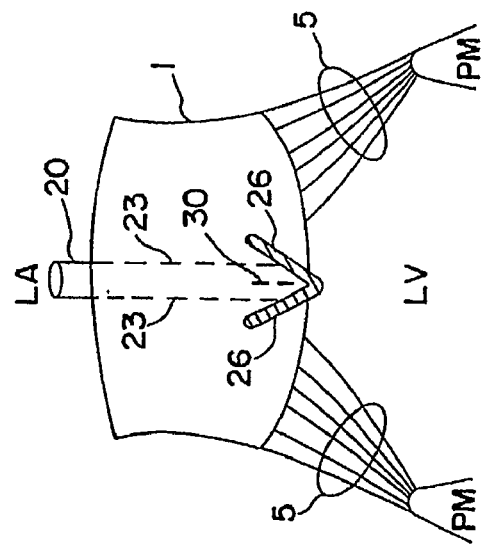
FIG. 3C is an illustration of a grasping element in accordance with the present invention showing two side-arms for stabilizing a portion of the leaflet surface so that a staple or rivet can be inserted therebetween, as viewed from above, looking down onto the upper surface of the anterior mitral leaflet.
Figure 3A:
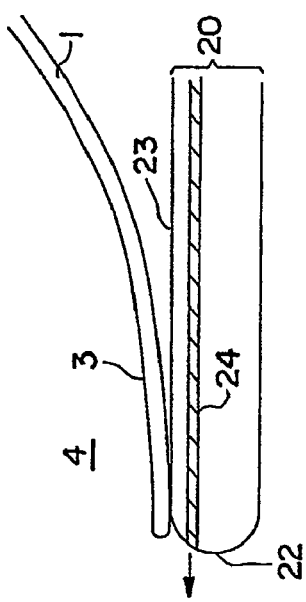

With reference to FIG. 3A, in one embodiment of the present invention a percutaneous catheter 20 is inserted through the interatrial septum into the left atrium 7 and then between the mitral leaflets (only anterior leaflet 1 shown) to the left ventricle 4 to a position adjacent leaflet 1 that is to be repositioned. Through catheter 20 at least one leaflet grasping element 24 can be reversibly extended from the catheter tip 22. The grasping element 24 is composed of a shape memory material that has been pre-formed to have a shape and dimensions appropriate for clipping or compressing leaflet 1 against the external surface 23 of the catheter 20, such as shown in FIG. 3B. When the grasping element 24 is extruded from the tip 22, the element takes its pre-formed shape, which as depicted can be a reverse curve 25 that results in a clip-like structure on the ventricular surface 3 of leaflet 1. The manufacturing of biocompatible shape memory components is well described in the art, thus will not be recited here.

FIG. 3C depicts a view of the mitral valve looking down onto the upper surface of the anterior mitral leaflet. Note that the device operates in this case in the gap between the chordal connections 5 to each side of the leaflet. In a preferred embodiment, the grasping element 24 has preferably two side arms 26 that extend to either side of the catheter axis in a V-shaped or similar configuration having a separation therebetween sufficient to allow a staple or rivet 30 to be inserted through the leaflet unopposed by the grasping element. This design provides greater stability than a single point of leaflet contact, and allows a staple or rivet 30 to be inserted between the side arms 26 of the grasping element without the leaflet being displaced in the process. The design also provides a relatively large, stabilized leaflet surface area against the external surface 23 of the catheter 20 and minimizes leaflet displacement during the process of staple or rivet fastening. An alternative embodiments includes the use of auxiliary suctioning ports on the catheter 20 to assist in the grasping process—these may be independently translatable.

Figures 4A, 4B, 4C, 5A:
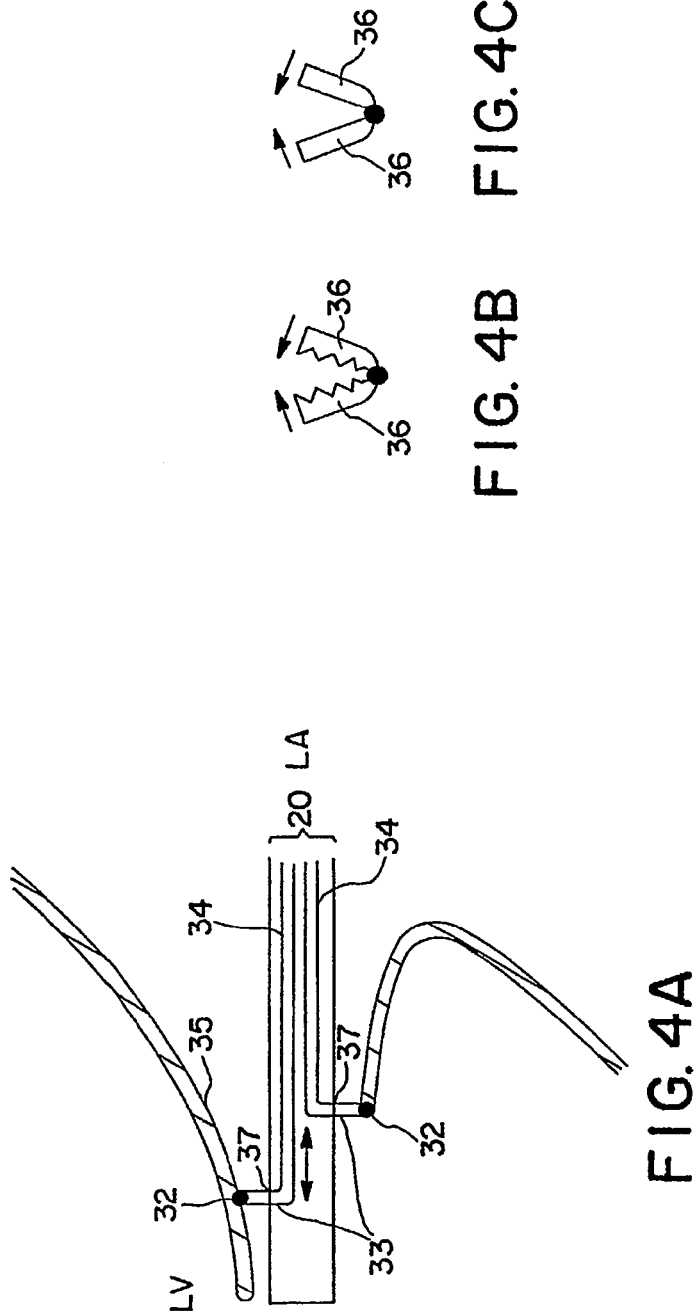
FIG. 4A is a side view illustration of a mechanism for grasping the atrial surface of the leaflets, with independent translation of two grabbing elements to approximate the leaflets.
FIGS. 4B,4C are schematic illustrations of serrated and smooth pincer-like grabbing tools disposed at the end of certain embodiments of the grasping elements.
FIG. 5A is a schematic illustration of a mechanism for inserting staples or rivets through an orifice in the catheter to fasten leaflets that have been approximated into apposition.

With reference to FIG. 4A, alternative embodiments of the grasping elements are each comprised of a control rod 34 having a steerable distal end 33, upon which is disposed a grabbing tool 32. A variety of mechanisms for steering percutaneous surgical instruments are known to artisans and may be employed in steering the distal end 33 so as to position the grabbing tool 32 adjacent a portion of the atrial surface 35 to be grasped. Each distal end 33 is extended and retracted through a side port 37 or groove in catheter 20. The grabbing tool 32, in one embodiment, has two pincer-like jaws 36 (two versions of which are shown in FIGS. 4B, 4C) that grasp the atrial surface 35 of the leaflet. One experienced in the art will recognize that a variety of other mechanisms currently available can be used as grabbing tools as an alternative to the jaws 36. One such alternative includes the use of suction tips combined with pincers, a design serving to improve leaflet-catheter contact but not requiring as high a suction rate such as needed to grasp both leaflets simultaneously, the suction herein being used only for fine positioning and alignment.

In another embodiment (not shown), more than one grasping element is employed to grasp the atrial surface of the leaflet. Multiple grasping elements extend in a similar direction away from the catheter to allow grasping of a selected axial length of the atrial surface. For example, there could be two grasping elements pointing to one side of the valve, and two to the other, thus stabilizing a square or rectangular portion of the leaflet surface.

In the embodiments described to this point, a single catheter 20 has been used to deliver and position the grasping elements to positions adjacent the ventricular or atrial surfaces of the leaflets. In a preferred embodiment, four independent grasping elements are used to grasp both surfaces of both leaflets, two elements per leaflet on opposite sides. This configuration provides the greatest flexibility in repositioning the leaflets into apposition and stabilizing them through the fastening step.

Figure 3E:
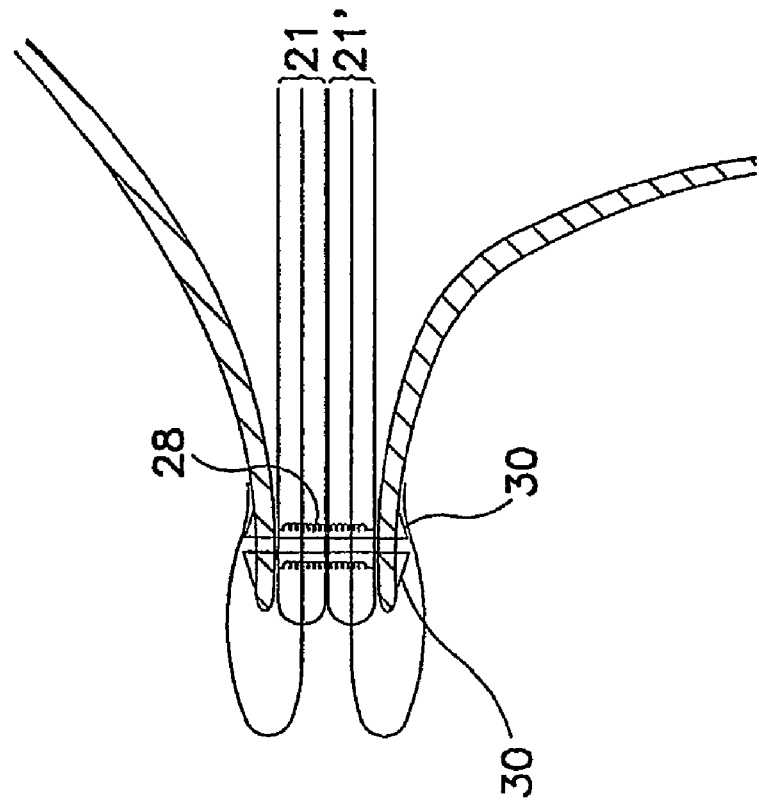
FIGS. 3D-3E are side view illustrations of a catheter assembly comprised of two linked catheters that independently translate grasped leaflets into apposition for fastening.
Figure 3D:
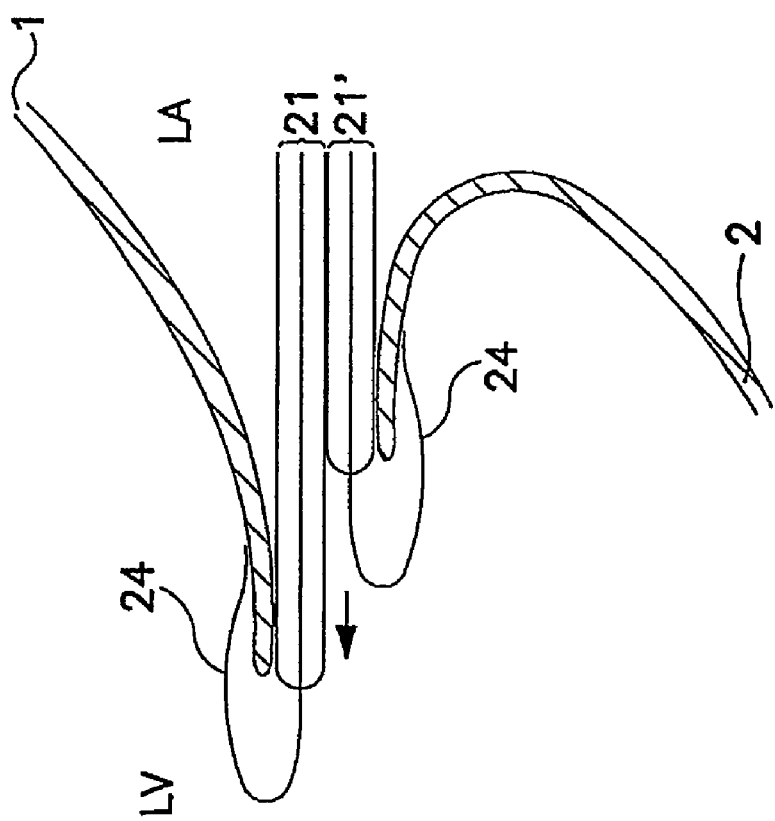

With reference to the alternative embodiment shown in FIGS. 3D and 3E, the grasping elements 24 may be delivered independently through separate but linked catheters 21,21'. The catheters 21,21' are linked, for example, by a tongue and groove configuration, that allows them to move in a common plane. Translating the catheters achieves the desired leaflet 1,2 approximation after the grasping step. Each of the catheters 21,21' in the catheter assembly has opening that together form a channel 28 through which the staple or rivet 30 is extended when the leaflets are repositioned in apposition.

As shown in FIG. 5A, once the leaflets 1,2 are grasped and approximated, one or more staples or rivets 30 are inserted through them. The staples or rivets 30 in one embodiment are composed of shape memory material and dimensioned to allow translation through the catheter 20 lumen and rapid expansion, effecting insertion and leaflet fastening, when the staples or rivets 30 reach an orifice 31 in the side wall of the catheter. The staples or rivets 30 are translated down the catheter 20 lumen by a plunger 29 until the orifice 31 is encountered. The staples or rivets 30 then emerge and pierce both leaflets, which have been previously stabilized by the grasping elements 24 described above. The shape memory staple or rivet emerges on the side of the leaflet opposite that of the catheter, and curves back to form a staple. Two or more such staples or rivets may be inserted at the same site, each facing in a different direction.

Figure 5C:
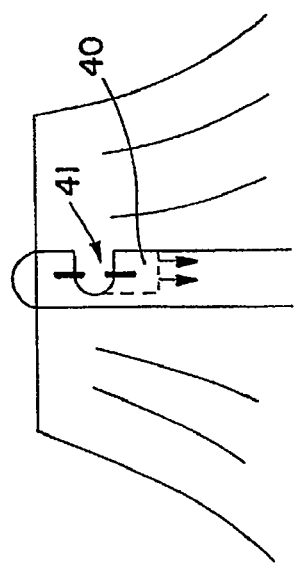
FIGS. 5B-5E are illustrations of operational steps for using a mechanism to disengage a staple from the catheter delivering it to the leaflet vicinity.
Figure 5E:
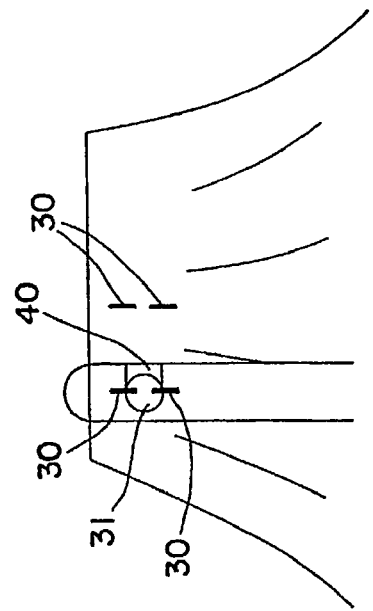
Figure 5B:
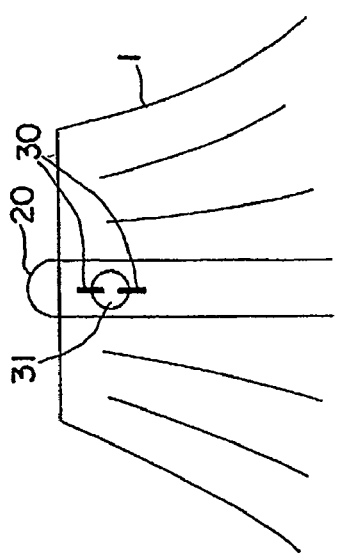

As shown in FIG. 5B, retractable door 40 in the side wall of the catheter can then be opened to disengage the catheter from the staples and move it to another site, so the leaflets can also be fastened together at additional locations to stabilize the repair, if necessary. After the catheter has been disengaged, the shape memory device continues to compress the leaflets together until an effective seal is formed.

Figure 5D:
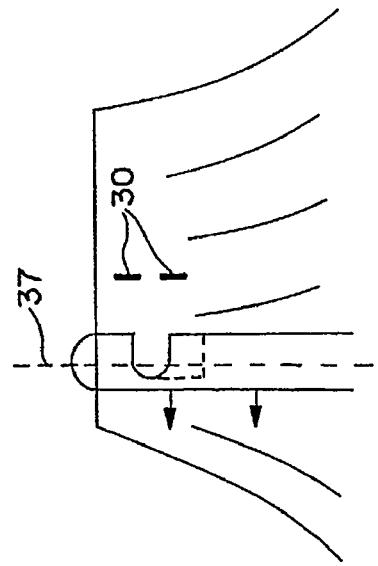

FIGS. 5B through 5E illustrate the sequence of maneuvers that achieve leaflet fastening at more than one site. In these figures, the cardiac valve is viewed from side to side as if looking down on its anterior leaflet 1 (as in the orientation shown in FIG. 3C.) Catheter 20 is depicted as entering from an atrial route, although the same process can be practiced with the catheter entering retrograde from the aorta. In FIG. 5B, staples or rivets 30 have been inserted through the orifice 31 in the catheter that allows their extrusion into the leaflets. Turning to FIG. 5C, a portion 40 of the side wall of the catheter is retracted into the catheter lumen, activated by a wire or other connection to the catheter controls outside the patient. This step opens a hole 41 in the side of the catheter. The catheter is then disengaged from the staple or riveting device, and translated parallel to the catheter axis 37. FIG. 5D shows the catheter translated to a position closer to one side of the leaflet. FIG. 5E shows the retractable catheter wall portion 40 replaced to re-form the piercing orifice 31 and allow fastening of the leaflets at another site. This can increase the efficacy of repair, as necessary, depending upon the precise geometry of the separated and regurgitant leaflets. This approach can be practiced with the linked sub-catheters shown in FIGS. 3D and 3E as well, using retractable wall portions for each sub-catheter. Retractable portions of the catheter side walls may be placed on both sides of the catheter to allow translation in either direction. After one staple has been placed, with slight adjustment of the angle of catheter approach, the disengaged catheter 20 may also be translated parallel to its axis 37 to insert additional staples at more than one site along the central axis of the left ventricle, which is parallel to the initial catheter axis.

With reference to FIGS. 6A, and 6B, an alternative embodiment inserts the catheter 20 retrograde into the left ventricle 4 through the aorta. The catheter is shaped or steered to curve back toward the mitral leaflet tips using shape memory materials or other steering mechanisms known in the art. An advantage of the present invention is the need for only a single catheter assembly due to the novel leaflet grasping elements, as opposed to catheters coming from both aortic and artial routes. Leaflet-grasping elements, after positioning, are then applied to the distal leaflet tips. The grasping elements 24 are extended forward from the catheter onto the ventricular sides of the leaflet to surround the leaflet between catheter and clip. This forward grasping may be achieved through a number of mechanisms. For example, the grasping elements 24 may be comprised of preformed shape memory material that compresses the leaflets upon extension from side ports in the catheter. Alternatively, the grasping elements may be comprised of more rigid members that are hinged upon control rods within a sock-like component that, when extended beyond the hinge point, urges the members back towards the catheter, encompassing a portion of the leaflet therebetween.

With reference to FIG. 6B, the entire process is preferably performed under the guidance of an imaging technique, such as echocardiography. Such guidance may be achieved using near infrared visualization (such as described in U.S. Pat. No, 6,178,346 incorporated herein by reference), with an intracardiac magnetic resonance imaging coil, or by transthoracic real-time three-dimensional echocardiographic imaging.

Ultrasound imaging may be performed from the chest surface, esophagus, or within the heart, using an independent intracardiac echo (ICE) catheter (commercially available) within the adjacent right ventricular outflow tract, or an ultrasound transducer within the left ventricle itself, built into the catheter 20. This arrangement allows an imaging element 50 to be maneuvered via the catheter to provide high-resolution images of the cardiac valve during the procedure, while also displaying the mitral leaflets and regurgitant jet. To produce a three-dimensional ultrasound image, a two-dimensional matrix array of piezoelectric crystals may be used, or a linear phased array may be rapidly rotated to produce a three-dimensional image.

The imaging may also be employed to confirm catheter contact with the leaflets and trigger the grasping step. The imaging element can be comprised of a simple piezoelectric crystal or optical coherence device that senses the motion of the leaflets. When the leaflet approaches the catheter in systole, the device outputs a triggering signal confirmable manually on an output display device. Once confirmed, the following triggering signal is output to a mechanism to translate the grasping element rapidly down the lumen to assume the retroflexing shape thereby effecting capture. In another embodiment, leaflet capture is effected by rapidly advancing a magnetic rod through the bore of the catheter to a position wherein the distal end of the extruded or extended grasping element, which in this embodiment is composed at least in part of a ferromagnetic material, is rapidly attracted toward the magnetic rod and the catheter. In yet another embodiment, a jointed rod is rapidly advanced so as to retroflex the grasping element against the leaflet.

Figure 7A:
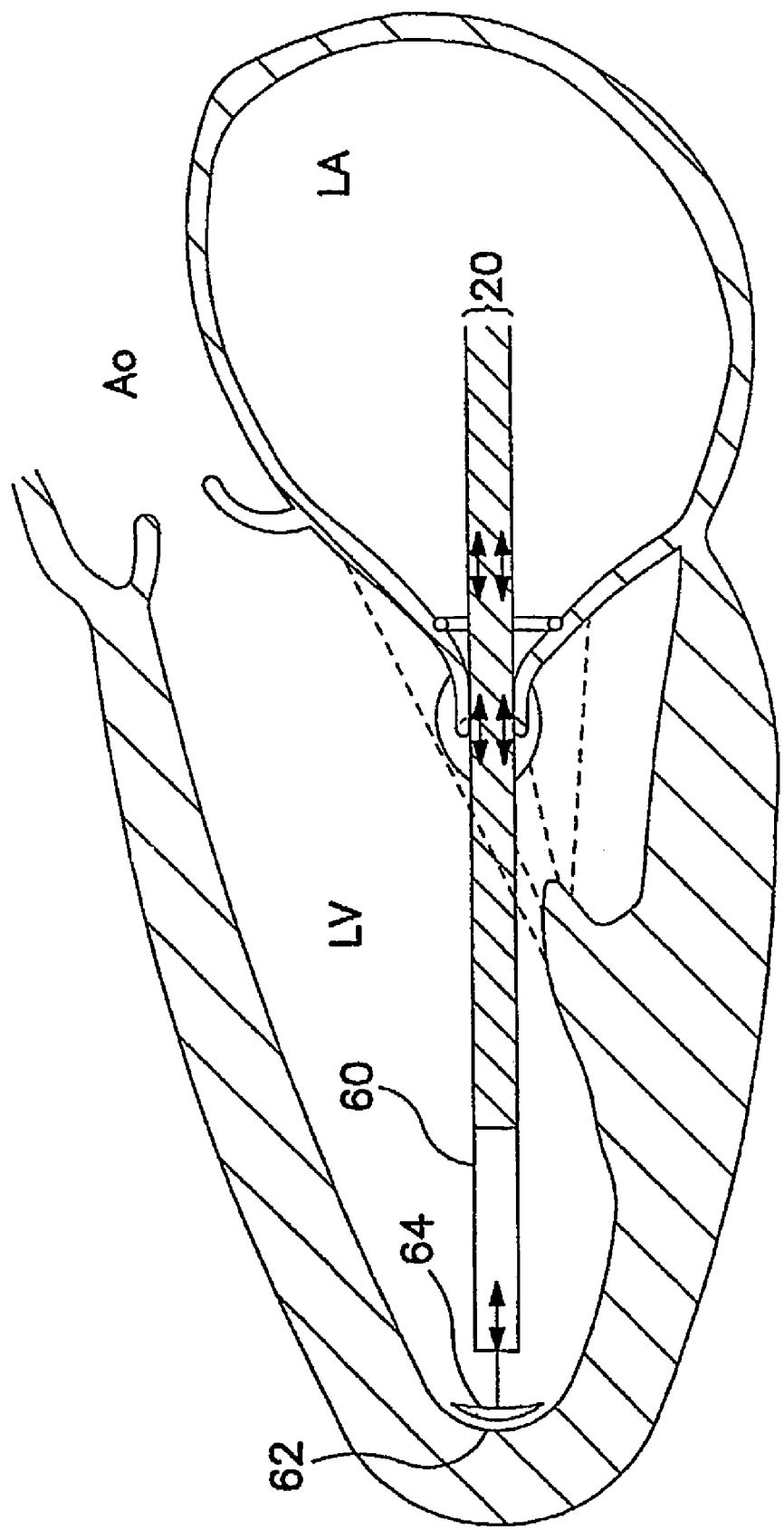

Both catheter introduction routes (through the mitral valve or the aorta) may also be practiced using a stabilizing catheter extension 60 advanced to the left ventricle apex 62, as shown in FIGS. 7A and 7B. From the extension 60 is extended a curving contact element 64 shaped to maintain contact with the apex 62. The contact element 64 may be made of shape memory elastic material which, when extruded from the catheter, forms a curving or tined contacting structure. Catheter 20 may then be translated along this wire to position the grasping elements 24,32 optimally in the region of the leaflet. For the transseptal route through the left atrium (FIG. 7A), the stabilizing catheter extension 60 is in continuity with the fastening catheter 20, while for retrograde aortic routes (FIG. 7B), the fastening catheter 20 emerges from an introducer catheter 64, and is steered toward the leaflets. The fastening catheter 20 is passed through a port in the introducer catheter 64, either directly or through a directing arm that may have an occlusive rubber seal. The introducer catheter 64 is stabilized by the curving contact element 64 extending beyond the catheter tip and shaped to maintain contact with the ventricular apex. The contact element 64 may alternatively be comprised of several elements composed of shape memory elastic material which, when extended from the catheter itself, form curving or tined contacting elements that may contact other portions of the interior of the cavity.

It is worth noting that the stabilizing mechanism described here is merely illustrative. The stabilizing mechanism is not limited to a wire or shape memory materials, nor is it limited to a single extendable contact element. For example, some embodiments may employ a plurality of stabilizing legs or telescoping extensions to contact inner left ventricle at numerous points around its circumference.

The device of this invention may also be practiced effectively in conjunction with procedures that assist in approximating the leaflets by inserting a mitral annular ring percutaneously. Such a device is inserted into the coronary sinus, a vein that encircles the mitral valve at the level of its annulus (the insertion of the leaflets onto the rest of the heart). Reducing annular size also helps in approximating the leaflets to achieve optimal repair. This combination of techniques utilizing the device of the present invention would provide a completely percutaneous approach to comprehensive repair of mitral valve prolapse and degenerative mitral regurgitation.

The present invention can also be used to treat ischemic mitral regurgitation in dilated hearts to reduce volume overload and prevent heart failure. Many of the more severe regurgitant lesions in such patients also involve malcoaption of non-apposed leaflet portions that can be repaired by this device. The present invention may be used with methods for reducing the tension on the leaflets to be so repaired, including percutaneous annular ring reductions and methods for reducing ventricular size. It can also be used to appose and link any two scallops of the posterior leaflet that may be malaligned or prolapse relative to each other, causing regurgitation.

While the foregoing specification has been described with regard to certain preferred embodiments, and many details have been set forth for the purpose of illustration, it will be apparent to those skilled in the art, that without departing from the spirit and scope of the invention, the invention may be subject to various modifications and additional embodiments, and that certain of the details described herein can be varied considerably without departing from the basic principles of the invention. Such modifications and additional embodiments are also intended to fall within the scope and spirit of the invention appended claims.

What is claimed is:

1. A device for repairing a cardiac valve, comprising:
   a catheter assembly configured to pass from the remote vasculature of a patient to a position within the heart adjacent the cardiac valve;
   at least two maneuverable grasping elements independently translatable through the catheter assembly, the grasping elements reversibly and radially extendable from the catheter assembly to capture and reposition portions of at least two valve leaflets into an apposed position; and
   a fastening mechanism translatable through the catheter assembly to secure the repositioned portions of the valve leaflets, wherein the catheter assembly is comprised of a plurality of slidably linked catheters, one of the grasping elements disposed in each catheter, and wherein each catheter includes at least one side port through which the fastening mechanism is extendable and disengagable from the catheter assembly.

2. A device for repairing a cardiac valve, comprising:
   a catheter assembly configured to pass from the remote vasculature of a patient to a position within the heart adjacent the cardiac valve;
   at least two maneuverable grasping elements independently translatable through the catheter assembly, the grasping elements reversibly and radially extendable from the catheter assembly to capture and reposition portions of at least two valve leaflets into an apposed position;
   a fastening mechanism translatable through the catheter assembly to secure the repositioned portions of the valve leaflets, wherein the fastening mechanism is radially extendable and disengagable from the catheter assembly through at least one side port of the catheter assembly; and a retractable portion of the catheter assembly, in its retracted state and proximate the at least one side port, creating an opening in the catheter assembly through which the fastening mechanism is disengagable from the catheter assembly.

3. A method for repairing a cardiac valve, comprising:

advancing a catheter assembly from the remote vasculature of a patient to a position within the heart adjacent the cardiac valve;

independently capturing and stabilizing in an apposed position, at locations relative to a particular axis of extension of the catheter assembly, at least two valve leaflets via at least two grasping elements translated through the catheter assembly, the locations capable of being axially different from one another with respect to the particular axis; and fastening the valve leaflets at one or more points; and disengaging the catheter assembly from the valve leaflets, wherein the capturing step comprises:

positioning each grasping element proximate the cardiac valve, reversibly and radially extending each of the grasping elements through one of at least two opposed side ports in the catheter assembly, steering each grasping element to a position proximate an atrial surface of one of the valve leaflets, and grasping the atrial surface.

4. The method of claim 3, wherein the catheter assembly is advanced via a pathway selected from the group consisting of: retrograde via the arterial system into the left ventricle, through the venous system and right atrium into the left atrium across the atrial septum, directly through a wall of the heart, and percutaneously through a small incision in the chest wall and pericardium.

5. The method of claim 3, wherein the capturing step comprises:

positioning each grasping element composed at least in part of shape memory material proximate the cardiac valve; and reversibly extruding the grasping elements from the catheter assembly, each grasping element reversibly and radially extending from the catheter assembly so as to clip a portion of one of the valve leaflets.

6. The method of claim 3, further comprising temporarily stabilizing the position of the catheter assembly within the heart.

7. The method of claim 3, further comprising the step of imaging a region near the cardiac valve during the repair method.

8. The method of claim 7, wherein the imaging comprises transducing ultrasound energy to the region.

9. The method of claim 8, wherein the ultrasound energy is transduced from the chest surface, esophagus, or within the heart.

10. The method of claim 8, wherein the ultrasound energy transduced from within the heart is provided by an ultrasound transducer positioned proximate the cardiac valve.

11. The method of claim 3, further comprising triggering the independent capturing of each leaflet based on sensor output indicating leaflet position.

12. A device for repairing a cardiac valve, comprising:

a catheter assembly configured to pass from the remote vasculature of a patient to a position within the heart adjacent the cardiac valve;

at least two maneuverable grasping elements independently translatable through the catheter assembly, the grasping elements reversibly and radially extendable from the catheter assembly to capture and reposition portions of at least two valve leaflets into an apposed position; and a fastening mechanism translatable through the catheter assembly to secure the repositioned portions of the valve leaflets, wherein the catheter assembly is comprised of a plurality of slidably linked catheters, one of the grasping elements disposed in each catheter, wherein each catheter includes at least one side port through which the fastening mechanism is extendable and disengagable from the catheter assembly, and wherein the grasping elements are substantially parallel to one another and extent in substantially the same plane.

* * * * *